(12) United States Patent
Servidio

(10) Patent No.: US 7,896,924 B1
(45) Date of Patent: Mar. 1, 2011

(54) UNICONDYLAR FEMORAL PROSTHETIC IMPLANT COMPONENT

(75) Inventor: Damon J. Servidio, Towaco, NJ (US)

(73) Assignee: Howmedica Osteonics Corp., Mahwah, NJ (US)

( * ) Notice: Subject to any disclaimer, the term of this patent is extended or adjusted under 35 U.S.C. 154(b) by 48 days.

(21) Appl. No.: 11/971,542

(22) Filed: Jan. 9, 2008

(51) Int. Cl.
*A61F 2/38* (2006.01)

(52) U.S. Cl. .................. 623/20.3; 623/20.14; 623/20.21; 623/20.35

(58) Field of Classification Search .............. 623/20.14, 623/20.18, 20.21, 20.3, 20.31, 20.28; 606/87, 606/88
See application file for complete search history.

(56) References Cited

U.S. PATENT DOCUMENTS

| | | | |
|---|---|---|---|
| 3,715,763 A | 2/1973 | Link | |
| 3,774,244 A | 11/1973 | Walker | |
| 3,852,830 A | 12/1974 | Marmor | |
| 3,953,899 A | 5/1976 | Charnley | |
| 4,034,418 A | 7/1977 | Jackson et al. | |
| 4,085,466 A | 4/1978 | Goodfellow et al. | |
| RE29,757 E | 9/1978 | Helfet | |
| 4,193,140 A | 3/1980 | Treace | |
| 4,207,627 A | 6/1980 | Cloutier | |
| 4,224,696 A | 9/1980 | Murray et al. | |
| 4,344,192 A | 8/1982 | Imbert | |
| 4,838,891 A | 6/1989 | Branemark et al. | |
| 4,944,756 A | 7/1990 | Kenna | |
| 5,035,700 A | 7/1991 | Kenna | |
| 5,037,439 A | 8/1991 | Albrektsson et al. | |
| 5,092,895 A | 3/1992 | Albrektsson et al. | |
| 5,207,711 A | 5/1993 | Caspari et al. | |
| 5,314,482 A | 5/1994 | Goodfellow et al. | |
| 5,336,266 A | 8/1994 | Caspari et al. | |
| 6,074,425 A | 6/2000 | Pappas | |
| 6,344,059 B1 | 2/2002 | Krakovits et al. | |
| 6,406,497 B2 | 6/2002 | Takei | |
| 6,494,914 B2 | 12/2002 | Brown et al. | |
| 6,503,280 B2 | 1/2003 | Repicci | |
| 6,554,866 B1 | 4/2003 | Aicher et al. | |
| 6,916,341 B2 | 7/2005 | Rolston | |
| 7,081,137 B1 | 7/2006 | Servidio | |
| 7,115,131 B2 | 10/2006 | Engh et al. | |
| 7,160,330 B2 | 1/2007 | Axelson, Jr. et al. | |
| 7,172,597 B2 | 2/2007 | Sanford | |
| 2004/0153162 A1 * | 8/2004 | Sanford et al. ............. | 623/20.3 |
| 2005/0197709 A1 | 9/2005 | Schaefer et al. | |

\* cited by examiner

*Primary Examiner*—David Isabella
*Assistant Examiner*—Yashita Sharma
(74) *Attorney, Agent, or Firm*—Arthur Jacob

(57) ABSTRACT

A unicondylar femoral prosthetic implant component for implant at a prepared implant site within a natural knee joint provides a femoral articular surface having a convex surface contour configuration along a femoral condylar surface in a restored knee joint. A relief section is located adjacent the anterior end of the femoral condylar surface for placement contiguous with the patella track of the natural knee joint. The relief section has a surface contour configuration dimensioned and configured for providing an essentially continuous and smooth transition between the patella track along the natural bone adjacent the implant site and the femoral condylar surface of the implant component. The surface contour configuration of the relief section preferably is concave.

11 Claims, 5 Drawing Sheets

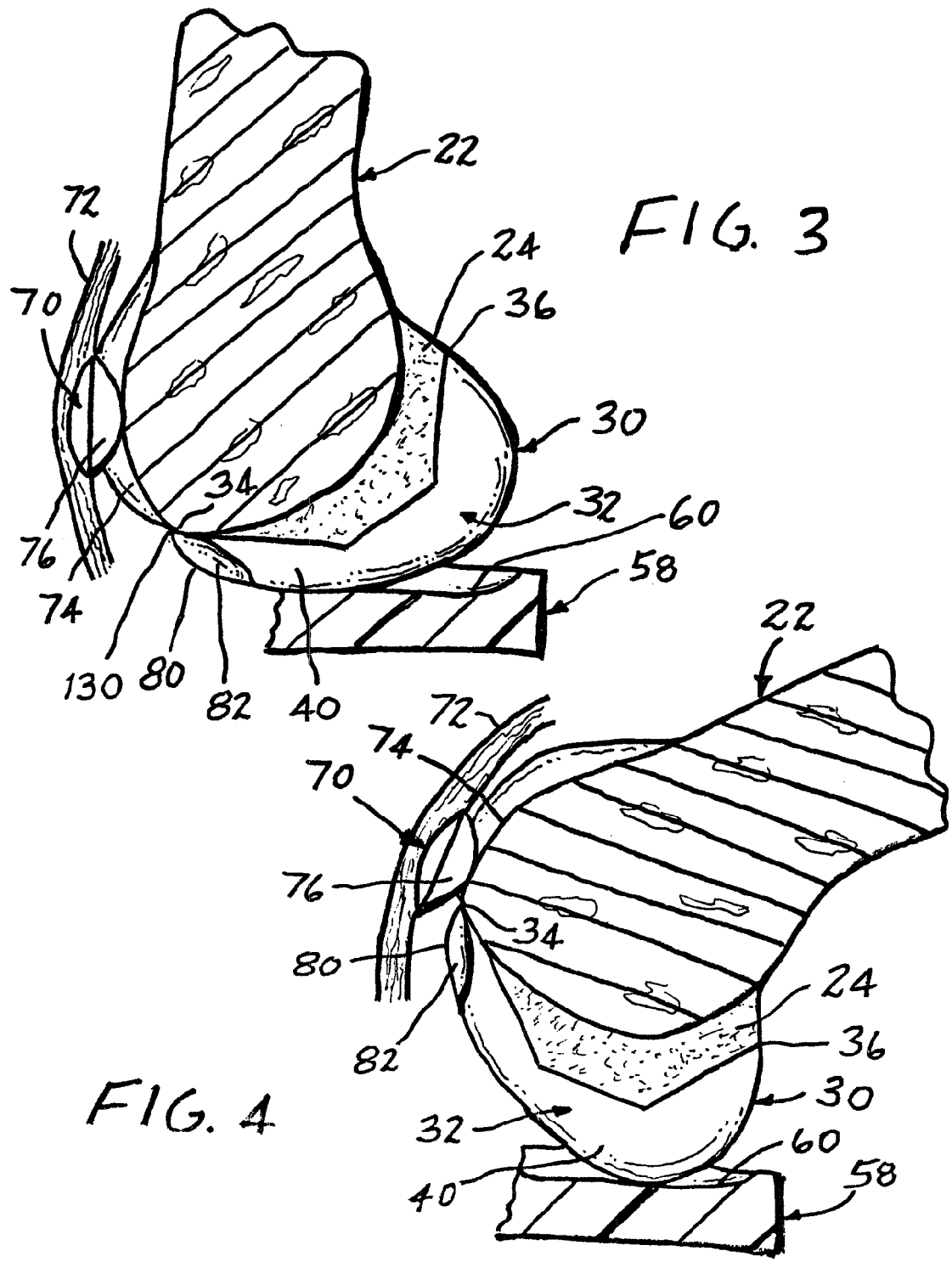

UNICONDYLAR FEMORAL PROSTHETIC IMPLANT COMPONENT

The present invention relates generally to prosthetic knee implant components and pertains, more specifically, to a unicondylar femoral prosthetic implant component having a section configured for better accommodation of the patella.

The natural knee includes articular surfaces located in each of three compartments, namely, a lateral compartment and a medial compartment within which femoral articular surfaces along the distal femur engage corresponding tibial articular surfaces along the proximal tibia, and a patella compartment placed between the condyles of the distal femur within which articular surfaces along the patella engage corresponding articular surfaces along the distal femur during flexion of the knee. Soft tissue surrounding the knee joint assists in stabilizing the knee during flexion while controlling internal rotation of the tibia and rollback of the femur, thereby driving the knee through natural knee kinematics.

The natural knee can become damaged, either through trauma or disease. In particular, damage to the articular surfaces, such as might result from arthritis, can impair the function of the natural knee and can cause discomfort and pain. Deficiencies in the articular surfaces of multiple compartments of the knee can be addressed through the implant of a total knee prosthesis offering a femoral component for providing condylar articular surfaces and a tibial component for providing tibial articular surfaces to be engaged by the condylar articular surfaces for restoring full knee function.

Where a deficiency is confined to a single compartment of the knee, a unicompartmental prosthesis can be employed to restore full knee function. Most current unicompartmental knee prostheses provide a unicondylar femoral component having a posterior articular surface which engages a relatively flat tibial articular surface to enable surrounding soft tissue to drive the prosthesis thorough movements designed to mimic natural knee kinematics. However, these current unicompartmental knee prostheses have been found not to fully mimic the natural anatomical relationships which accommodate articulation along the patella articular surfaces during flexion of the knee joint. In particular, experience has shown that in deep flexion, a transition between the natural bone and the unicondylar implant, along the patella track, can interfere with smooth articulation along the patella articular surfaces. Surgical compromises designed to overcome the problem generally have met with negative clinical results.

The present invention provides a unicondylar femoral prosthetic implant component which addresses articulation along the patella articular surfaces, especially in deep flexion. As such, the present invention attains several objects and advantages, some of which are summarized as follows: Provides a unicondylar femoral prosthetic implant component which enables articulation along patella articular surfaces to mimic articulation along the patella articular surfaces in a natural knee during flexion, and especially through deep flexion; better accommodates articulation along the patella articular surfaces in a unicompartmental knee prostheses; accomplishes exemplary clinical results in a unicompartmental knee prosthesis, with greater ease and increased precision; avoids the necessity for surgical compromises in the implant of a unicondylar prosthetic implant component for accommodating articulation along patella articular surfaces during deep flexion; allows greater latitude for attaining more satisfactory results in connection with the implant of a unicondylar prosthetic implant component; provides an increased range of articulation in a unicomparmental knee prosthesis with greater comfort; enables exemplary performance over an extended service life.

The above objects and advantages, as well as further objects and advantages, are attained by the present invention which may be described briefly as a unicondylar femoral prosthetic implant component for implant at a prepared implant site within a natural knee joint having a lateral compartment, a medial compartment and a patella compartment intermediate the lateral compartment and the medial compartment, the patella compartment including a patella track, the implant site being located within one of the lateral compartment and the medial compartment, adjacent the patella compartment and the patella track, the unicondylar femoral prosthetic implant component comprising: a femoral condylar surface extending along the implant component between an anterior end and a posterior end of the femoral condylar surface, the femoral condylar surface including a femoral articular surface; and a seating surface for seating the implant component upon natural bone at the prepared implant site to establish a restored knee joint with the femoral articular surface in place for engaging a corresponding tibial articular surface during flexion of the restored knee joint; the femoral condylar surface including a relief section located adjacent the anterior end of the femoral condylar surface for placement contiguous with the patella track, the relief section having a surface contour configuration dimensioned and configured for providing an essentially continuous transition between the patella track along natural bone adjacent the implant site and the femoral condylar surface, thereby enabling engagement of the patella along the patella track and along the femoral condylar surface of the restored knee joint during flexion of the restored knee joint to better mimic engagement of the patella along the patella track of the natural knee joint during flexion of the natural knee joint.

The invention will be understood more fully, while still further objects and advantages will become apparent, in the following detailed description of preferred embodiments of the invention illustrated in the accompanying drawing, in which:

FIG. 3 is a largely diagrammatic cross-sectional view taken along line 3-3 of FIG. 2 and showing the implant component implanted at the implant site;

FIGS. 4 and 5 are views similar to FIG. 3 and showing the knee joint at different degrees of flexion;

Figure 7:
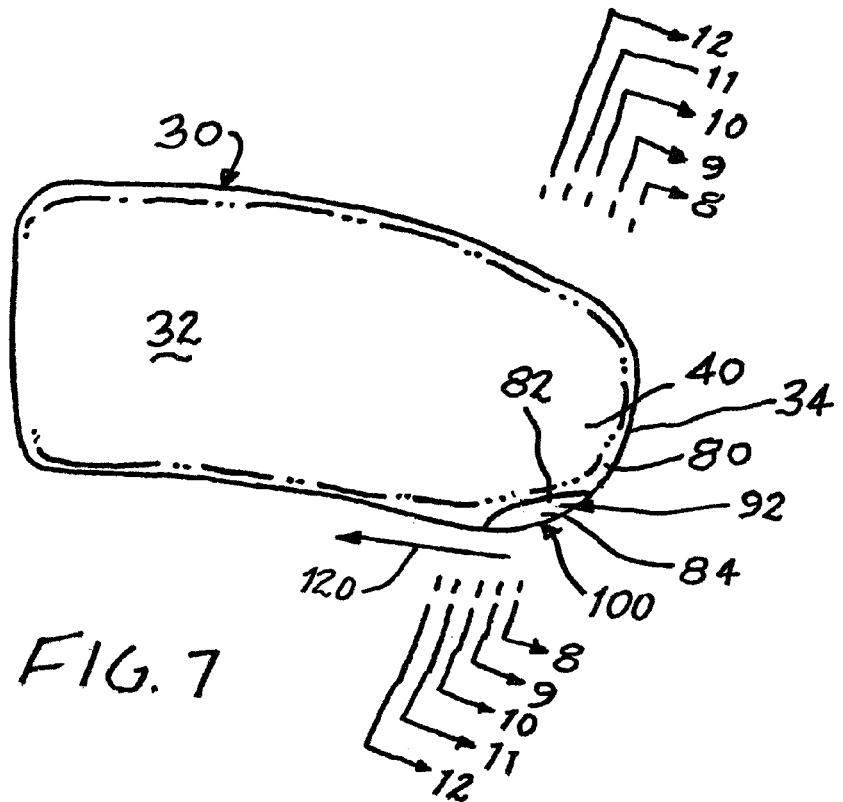
FIG. 7 is bottom plan view of the implant component.
Figure 8:
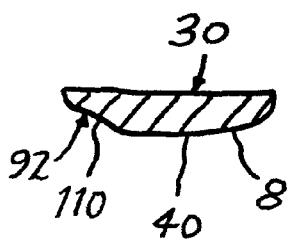
Figure 9:
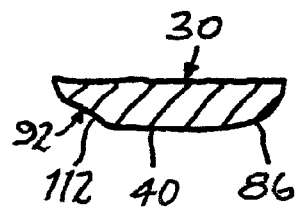
Figure 10:
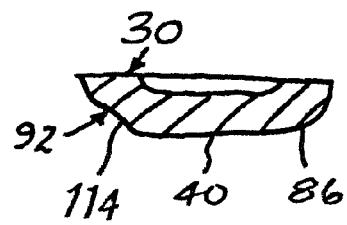
Figure 11:
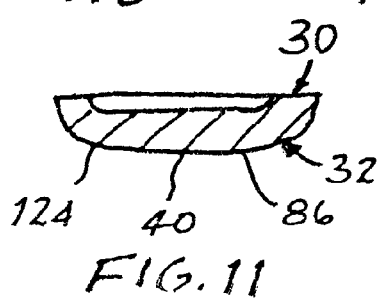
Figure 12:
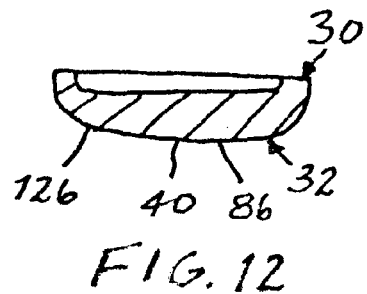

FIGS. 8 through 12 are cross-sectional views taken along corresponding lines 8-8 through 12-12 in FIG. 7.

Figure 1:
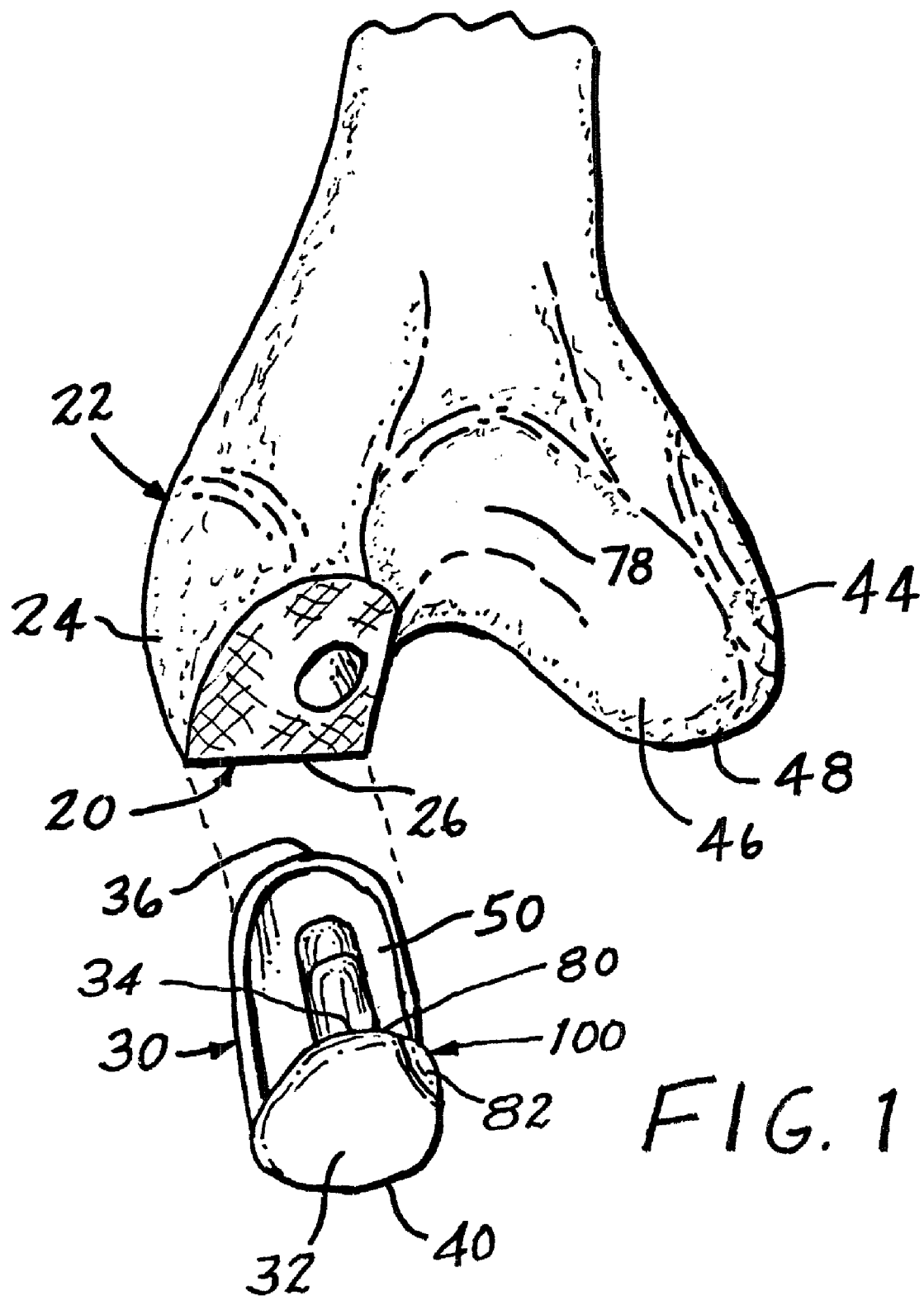
FIG. 1 is an exploded pictorial perspective view showing a unicondylar femoral prosthetic implant component constructed in accordance with the present invention and about to be implanted at an implant site.

Referring now to the drawing, and especially to FIG. 1 thereof, an implant site 20 at a distal femur 22 has been prepared along the medial condyle 24 within the medial compartment 26 of the distal femur 22 for the reception of a unicondylar femoral prosthetic implant component 30 constructed in accordance with the present invention. Once implanted, implant component 30 will provide the distal femur 22 with a femoral condylar surface 32 extending along implant component 30 between an anterior end 34 and a posterior end 36 of the femoral condylar surface 32, the femoral condylar surface 32 having a femoral articular surface 40 which will replace a damaged femoral articular surface along the medial condyle 24 within the medial compartment 26. The lateral condyle 44 which lies within lateral compartment 46 includes an undamaged femoral articular surface 48 and requires no repair. A seating surface 50 enables the implant component 30 to be seated upon natural bone at the prepared implant site 20 for affixation to the bone in a now conventional manner in the restoration of a damaged knee joint.

Figure 2:
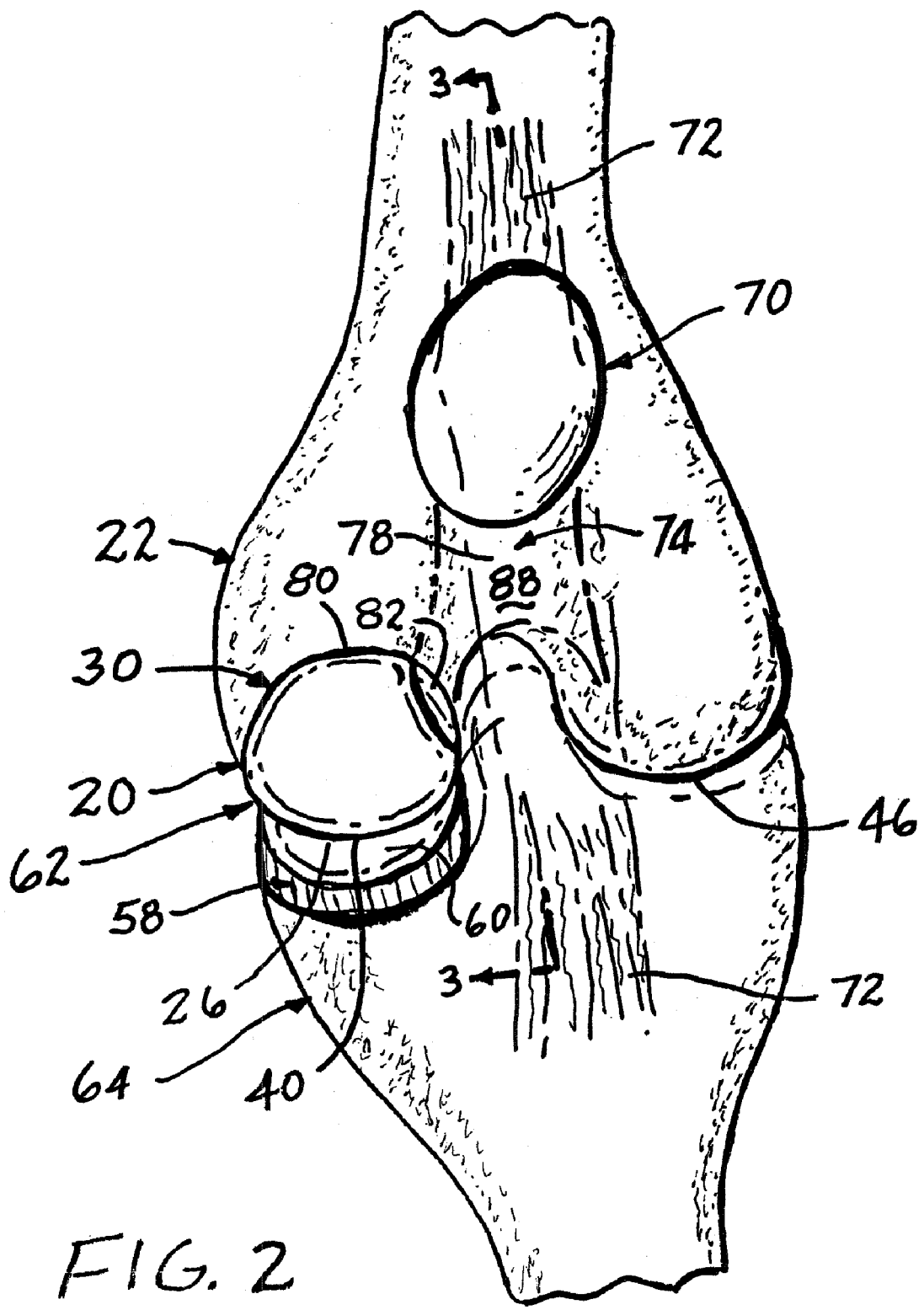
FIG. 2 is a pictorial perspective view showing the component implanted in a restored knee joint.

As seen in FIGS. 2 and 3, once seated and secured at the implant site 20, the implant component 30 is engaged with a tibial component 58, with femoral articular surface 40 in place for engaging corresponding tibial articular surface 60 of tibial component 58, in a restored knee joint 62 at the distal femur 22 and the proximal tibia 64. During flexion of the restored knee joint 62, the patella 70, which itself is held in place by corresponding soft tissue 72, will engage patella track 74, along patella articular surfaces 76, within patella compartment 78 located between the medial compartment 26 and the lateral compartment 46 of the knee. As the restored knee joint 62 is flexed through ordinary movements, such as walking and climbing and descending stairs, flexion takes place between full extension, as illustrated diagrammatically in FIG. 3, and about 60° of flexion, as shown diagrammatically in FIG. 4, and the patella articular surfaces 76 of patella 70 remain engaged with natural bone along the patella track 74. However, upon deep flexion, that is, beyond about 90° of flexion and up to about 120° of flexion, as depicted in FIG. 5, an articular surface 76 of patella 70 will engage an anterior portion 80 of implant component 30, the anterior portion 80 being contiguous with natural bone along the patella track 74.

Figure 5:
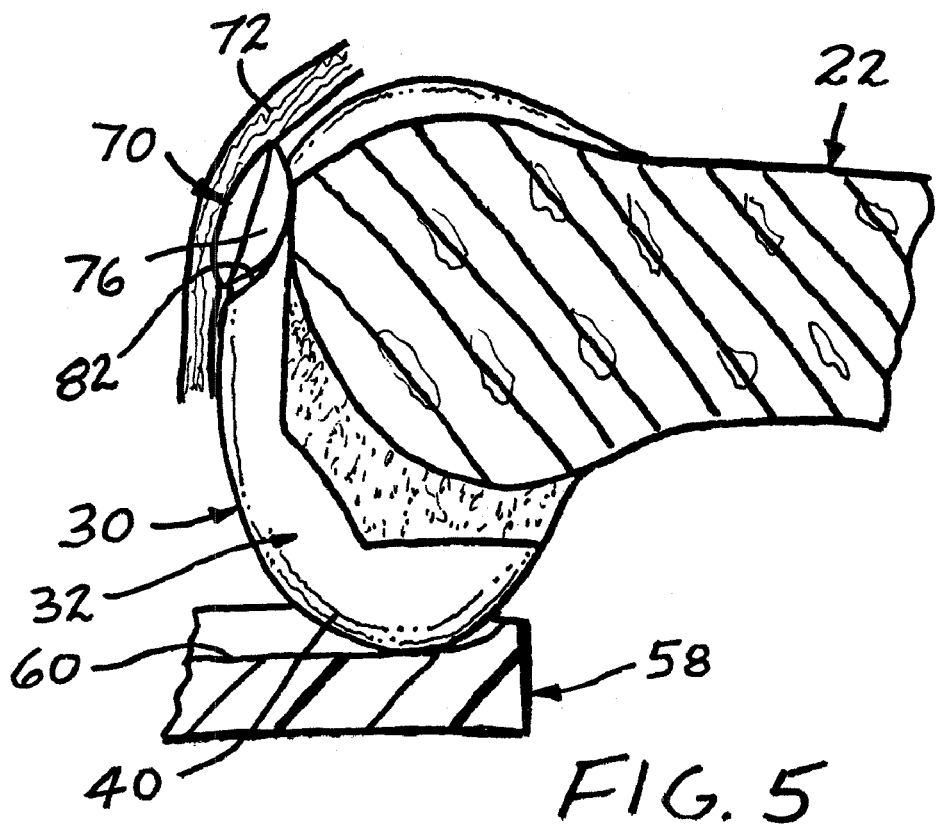
Figure 6:
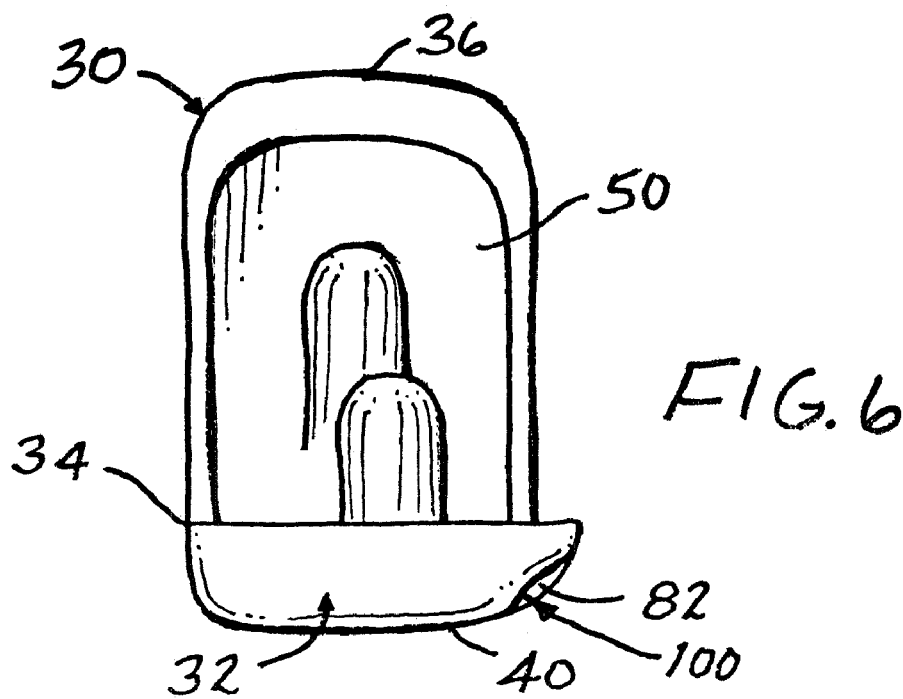
FIG. 6 is a front elevational view of the implant component.

Turning now to FIGS. 6 through 12, as well as to FIGS. 3 through 5, in order to assure a smooth and uninterrupted transition between the natural bone and the anterior portion 80 of implant component 30 as the articular surface 76 of patella 70 traverses the patella track 74, and thereby more faithfully mimic the kinematics of the natural knee, the femoral condylar surface 32 is provided with a relief section 82 having a relief surface 84 at the anterior portion 80 of the implant component 30. While the femoral articular surface 40 provided by the femoral condylar surface 32 of the implant component 30 has a generally convex surface contour configuration 86 for essentially replicating the contour configuration of the replaced natural femoral articular surface, the contour configuration along the surface of patella track 74 is concave. In deep flexion, where patella articular surface 76 will be engaged by the anterior portion 80 of implant component 30, an immediate transition from the concave contour configuration of the patella track 74 to the convex contour configuration 86 along the femoral articular surface 40 of the implant component 30 could result in an unwanted abrupt change in the location of the patella 70, causing some dislocation of the patella 70 from a natural position, with concomitant discomfort and pain experienced by the recipient of the restored knee joint 62.

In order to avoid such an unwanted abrupt change, relief surface 84 along anterior portion 80 is provided with a surface contour configuration 92 which is configured along a medial-anterior corner 100 of the implant component 30 and which gradually merges with the convex surface contour configuration 86 of femoral articular surface 40. Thus, the surface contour configuration of relief surface 84, as depicted at 92 in FIGS. 7 through 10, progresses from a preferred concave cross-sectional configuration illustrated at 110 in FIG. 8 to a preferred concave cross-sectional configuration shown at 112 in FIG. 9, and then to a preferred concave cross-sectional configuration depicted at 114 in FIG. 10, to emulate the surface contour configuration of the contiguous patella track 74, relief surface 84 diminishing in area along the direction 120 extending away from the anterior end 34 of the femoral condylar surface 32. Beyond the relief surface 84, in the direction 120, the surface contour configuration 86 becomes entirely essentially convex, as illustrated at 124 in FIG. 11 and then at 126 in FIG. 12, merging smoothly with femoral articular surface 40. In this manner, as the restored knee joint 62 is moved into and out of deep flexion, an essentially continuous transition is provided between the patella track 74 along the natural bone adjacent the implant site 20 and the femoral condylar surface 32, thereby enabling engagement of the corresponding patella articular surface 76 along the patella track 74 and along the femoral condylar surface 32 of the restored knee joint 62 to better mimic engagement of the patella articular surface 76 along the patella track of the natural knee joint. Note that the abrupt change at 130 (see FIG. 3) between the contour configuration of the femoral condylar surface 32 and the surface of the natural bone contiguous with the implant component 30 lies outside the patella track 74 and will not have a negative effect on the kinematics of the restored knee joint 62.

While the illustrated implant component 30 is shown implanted in the medial compartment 26, for repair of the articular surface of the medial condyle 24, the lateral condyle 44 may be repaired, as necessary, in the same manner as described above, utilizing an implant component constructed in the form of a mirror-image of implant component 30, for implant in the lateral condyle 44 within lateral compartment 46.

It will be seen that the present invention attains all of the objects and advantages summarized above, namely: Provides unicondylar femoral prosthetic implant component which enables articulation along patella articular surfaces to mimic articulation along the patella articular surfaces in a natural knee during flexion, and especially through deep flexion; better accommodates articulation along the patella articular surfaces in a unicompartmental knee prostheses; accomplishes exemplary clinical results in a unicompartmental knee prosthesis, with greater ease and increased precision; avoids the necessity for surgical compromises in the implant of a unicondylar prosthetic implant component for accommodating articulation along patella articular surfaces during deep flexion; allows greater latitude for attaining more satisfactory results in connection with the implant of a unicondylar prosthetic implant component; provides an increased range of articulation in a unicomparmental knee prosthesis with greater comfort; enables exemplary performance over an extended service life.

It is to be understood that the above detailed description of preferred embodiments of the invention is provided by way of example only. Various details of design and construction may be modified without departing from the true spirit and scope of the invention, as set forth in the appended claims.

The embodiments of the invention in which an exclusive property or privilege is claimed are defined as follows:

1. A unicondylar femoral prosthetic implant component for implantation at a prepared implant site within a natural knee joint having a lateral compartment, a medial compartment and a patella compartment intermediate the lateral compartment and the medial compartment, the patella compartment including a patella track, the implant site being located within one of the lateral compartment and the medial compartment, adjacent the patella compartment and the patella track, the unicondylar femoral prosthetic implant component comprising:

a femoral condylar surface extending along the implant component between an anterior end and a posterior end of the femoral condylar surface, the femoral condylar surface including a femoral articular surface having an anterior portion for being contiguous with the natural bone track along the patella track; and a seating surface for seating the implant component upon natural bone at the prepared implant site to establish a restored knee joint with the femoral articular surface in place for engaging a corresponding tibial articular surface during flexion of the restored knee joint;

the femoral condylar surface including a relief section located adjacent the anterior end of the femoral condylar surface for placement contiguous with the patella track, the femoral condylar surface continuing along the relief section, following a smooth and continuous surface contour configuration extending from the seating surface, adjacent the anterior end of the femoral condylar surface, posteriorly to the femoral articular surface for providing an essentially continuous smooth and uninterrupted transition between the patella track along natural bone adjacent the implant site and the femoral condylar surface and gradually merging with the femoral articular surface, thereby enabling engagement of the patella along the patella track and along the femoral condylar surface of the restored knee joint during flexion of the restored knee joint to better mimic engagement of the patella along the patella track of the natural knee joint and militate against dislocation of the patella during flexion of the natural knee joint through deep flexion.

2. The implant component of claim 1 wherein the femoral articular surface includes a convex surface contour configuration and the surface contour configuration of the relief section is generally concave.

3. The implant component of claim 2 wherein the implant component is configured for placement in the medial compartment and the relief section is located at an anterior and lateral corner of the implant component.

4. The implant component of claim 2 wherein the implant component is configured for placement in the lateral compartment and the relief section is located at an anterior and medial corner of the implant component.

5. The implant component of claim 1 wherein the implant component is configured for placement in the medial compartment and the relief section is located at an anterior and lateral corner of the implant component.

6. The implant component of claim 1 wherein the implant component is configured for placement in the lateral compartment and the relief section is located at an anterior and medial corner of the implant component.

7. The implant component of claim 1 wherein the relief section is located on the implant component such that upon implantation of the implant component at the implant site, the relief section will be placed for engagement by the patella during deep flexion of the restored knee.

8. The implant component of claim 7 wherein the relief section is located on the implant component such that upon implantation of the implant component at the implant site, the relief section will be placed for engagement by the patella during flexion of the restored knee between about 90° and about 120° of flexion.

9. The implant component of claim 8 wherein the femoral articular surface includes a convex surface contour configuration and the surface contour configuration of the relief section is generally concave.

10. The implant component of claim 9 wherein the implant component is configured for placement in the medial compartment and the relief section is located at an anterior and lateral corner of the implant component.

11. The implant component of claim 9 wherein the implant component is configured for placement in the lateral compartment and the relief section is located at an anterior and medial corner of the implant component.

* * * * *